US010087136B2

(12) United States Patent
Brenna et al.

(10) Patent No.: US 10,087,136 B2
(45) Date of Patent: Oct. 2, 2018

(54) PROCESS FOR THE PREPARATION OF METARAMINOL

(71) Applicant: LABORATORI ALCHEMIA S.R.L., Milan (IT)

(72) Inventors: Davide Brenna, Senago (IT); Andrea Marchesi, Bergamo (IT); Voichita Mihali, Milan (IT)

(73) Assignee: LABORATORI ALCHEMIA S.R.L., Milan (IT)

( * ) Notice: Subject to any disclaimer, the term of this patent is extended or adjusted under 35 U.S.C. 154(b) by 16 days.

(21) Appl. No.: 15/414,993

(22) Filed: Jan. 25, 2017

(65) Prior Publication Data
US 2017/0210696 A1    Jul. 27, 2017

(30) Foreign Application Priority Data

Jan. 26, 2016   (IT) ........................ 102016000007568

(51) Int. Cl.
*C07C 213/02*    (2006.01)

(52) U.S. Cl.
CPC ........ *C07C 213/02* (2013.01); *C07B 2200/07* (2013.01)

(58) Field of Classification Search
None
See application file for complete search history.

(56) References Cited

FOREIGN PATENT DOCUMENTS

| CN | 103739504 | * | 4/2014 |
| CN | 103739504 A |  | 4/2014 |

OTHER PUBLICATIONS

CN-103739504 machine translation, published Apr. 23, 2014.*
Bray et al. Chem. Eur. J. 2008, 14, 4725-4730.*
Search Report (and written opinion) of corresponding European Application No. 17152814.4 dated Jun. 21, 2017.
Search Report (and written opinion) of Italian priority Application No. 102016000007568 dated Sep. 14, 2016.
Gonzalo Blay et al "New Highly asymmetric Henry reaction catalyzed by CuII and aC1-Symmetric Aminopyridine Ligand, and Its Application to the Synthesis of Miconazole" Chemistry—A European Journal.

* cited by examiner

*Primary Examiner* — Clinton A Brooks

(57) ABSTRACT

Object of the invention is a process for the preparation of Metaraminol and the salts thereof, in particular its pharmaceutically acceptable salts, especially Metaraminol bi-L-tartrate. Object of the invention is also the use of a novel catalyst and a novel ligand for the synthesis of Metaraminol and its salts.

16 Claims, 15 Drawing Sheets

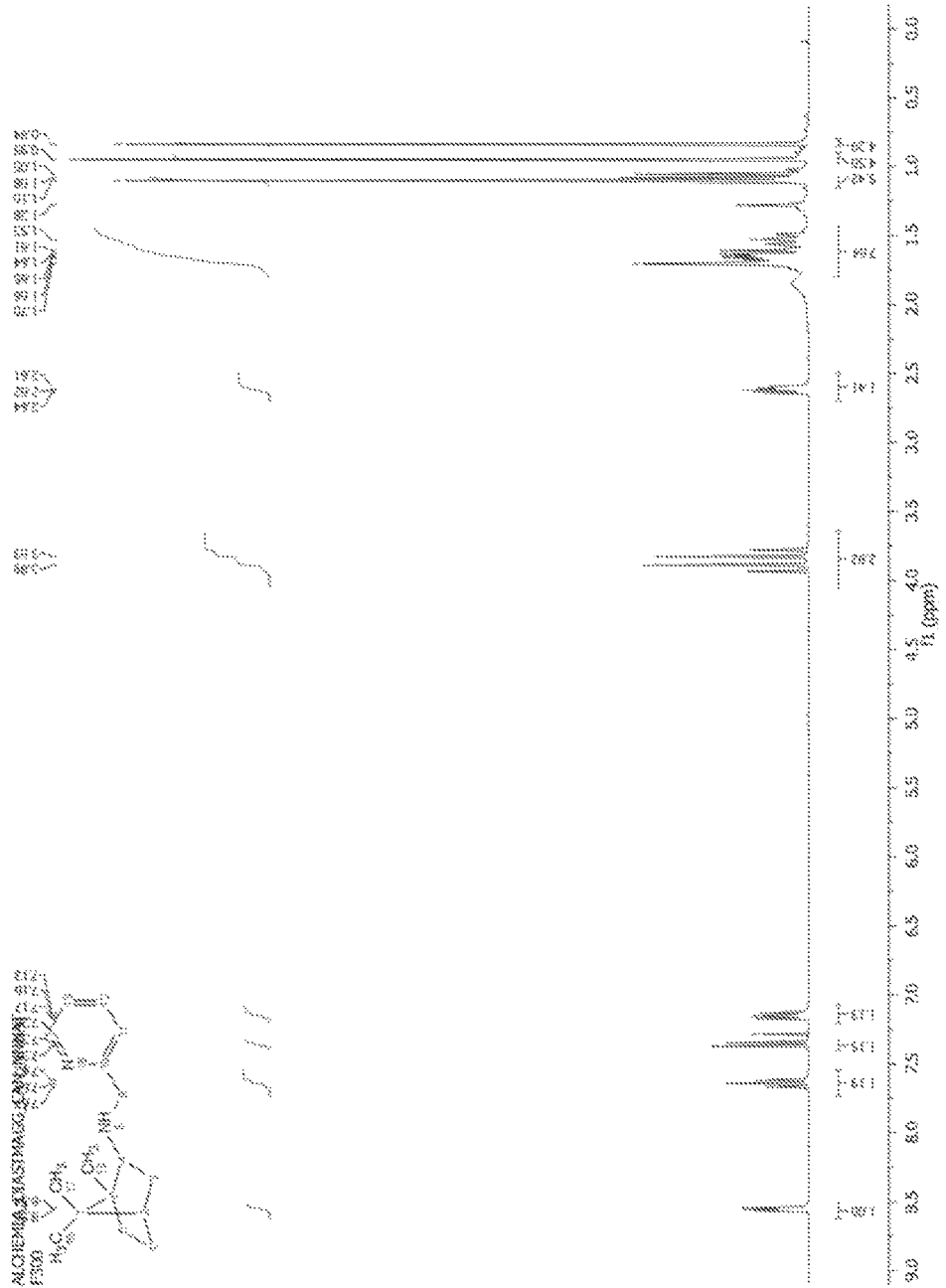
Figure 1: $^1$H-NMR spectrum of the compound of formula (III)

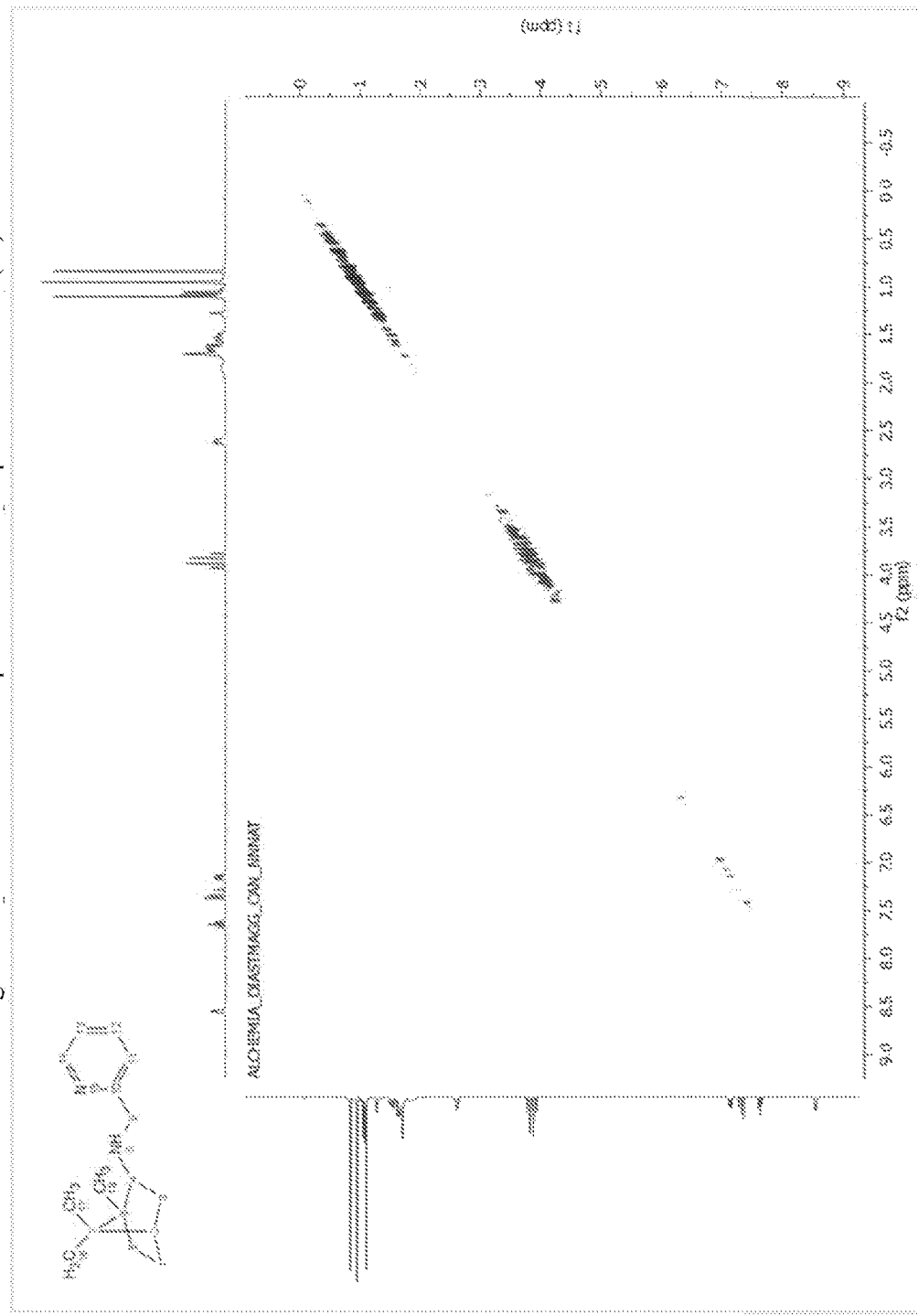
Figure 2: Bidimensional NMR spectrum of the compound of formula (III)

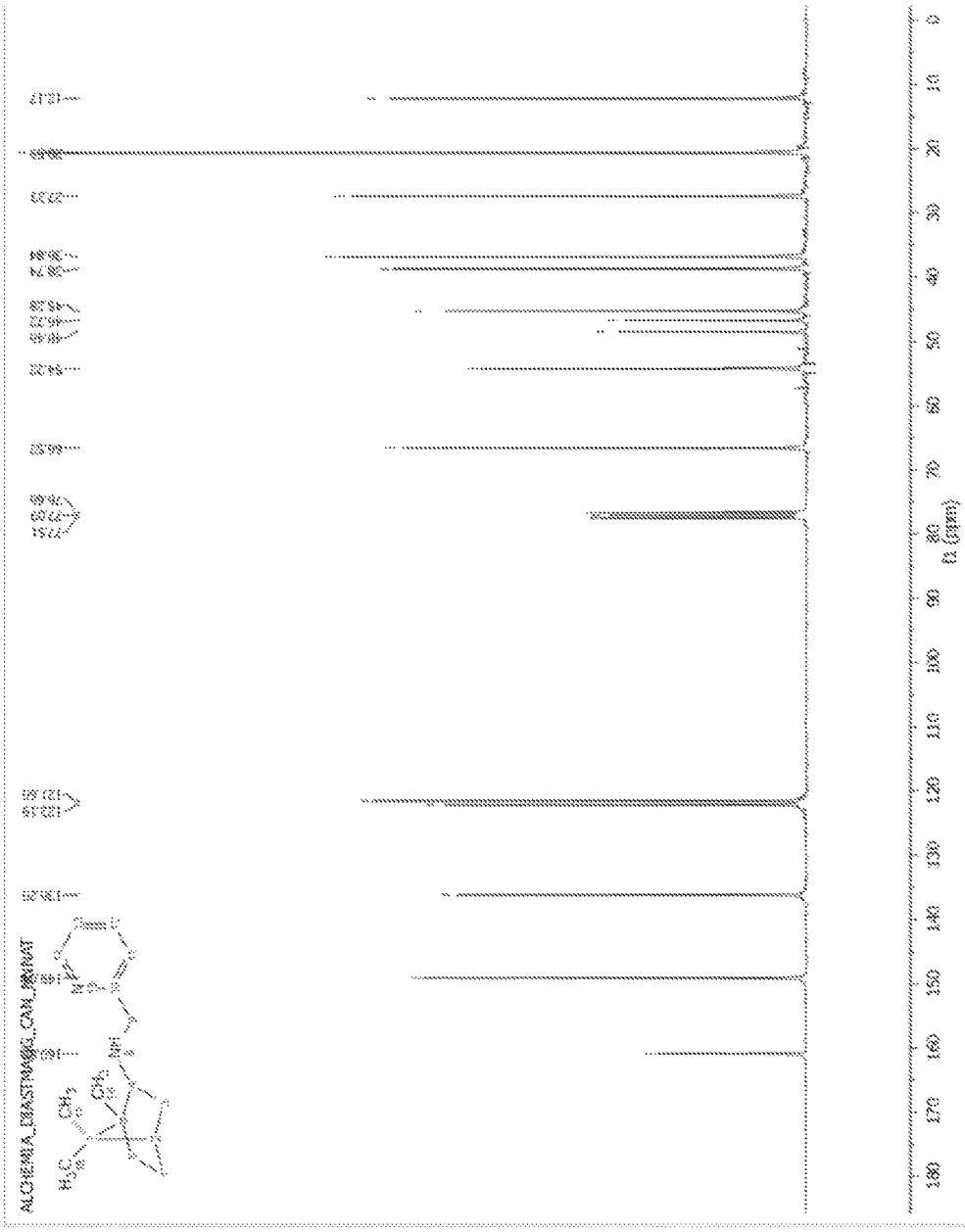

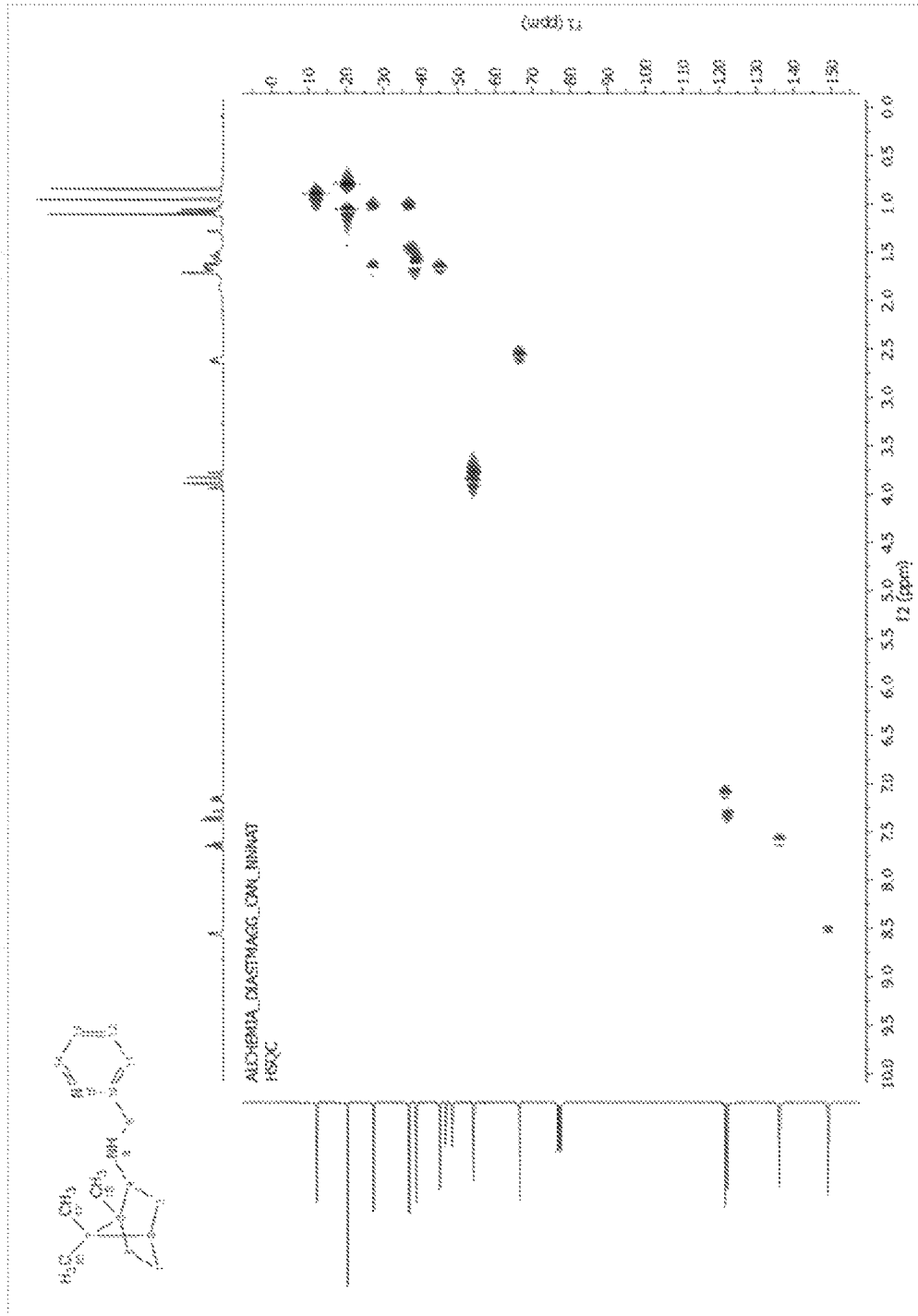
Figure 4: $^1$H-NMR/$^{13}$C heterocorrelated spectrum of the compound of formula (III)

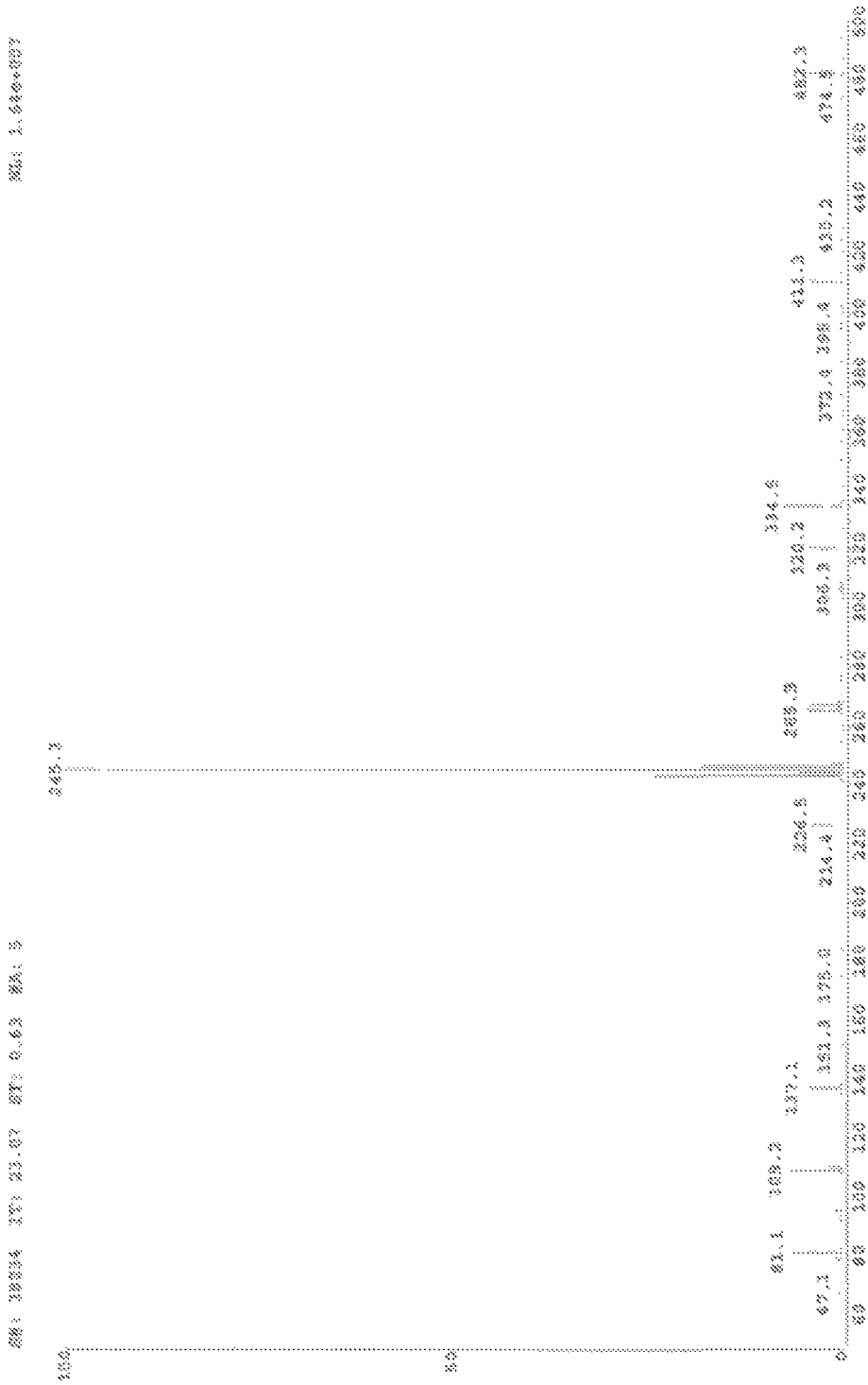
Figure 5: Mass spectrum of the compound of formula (III)

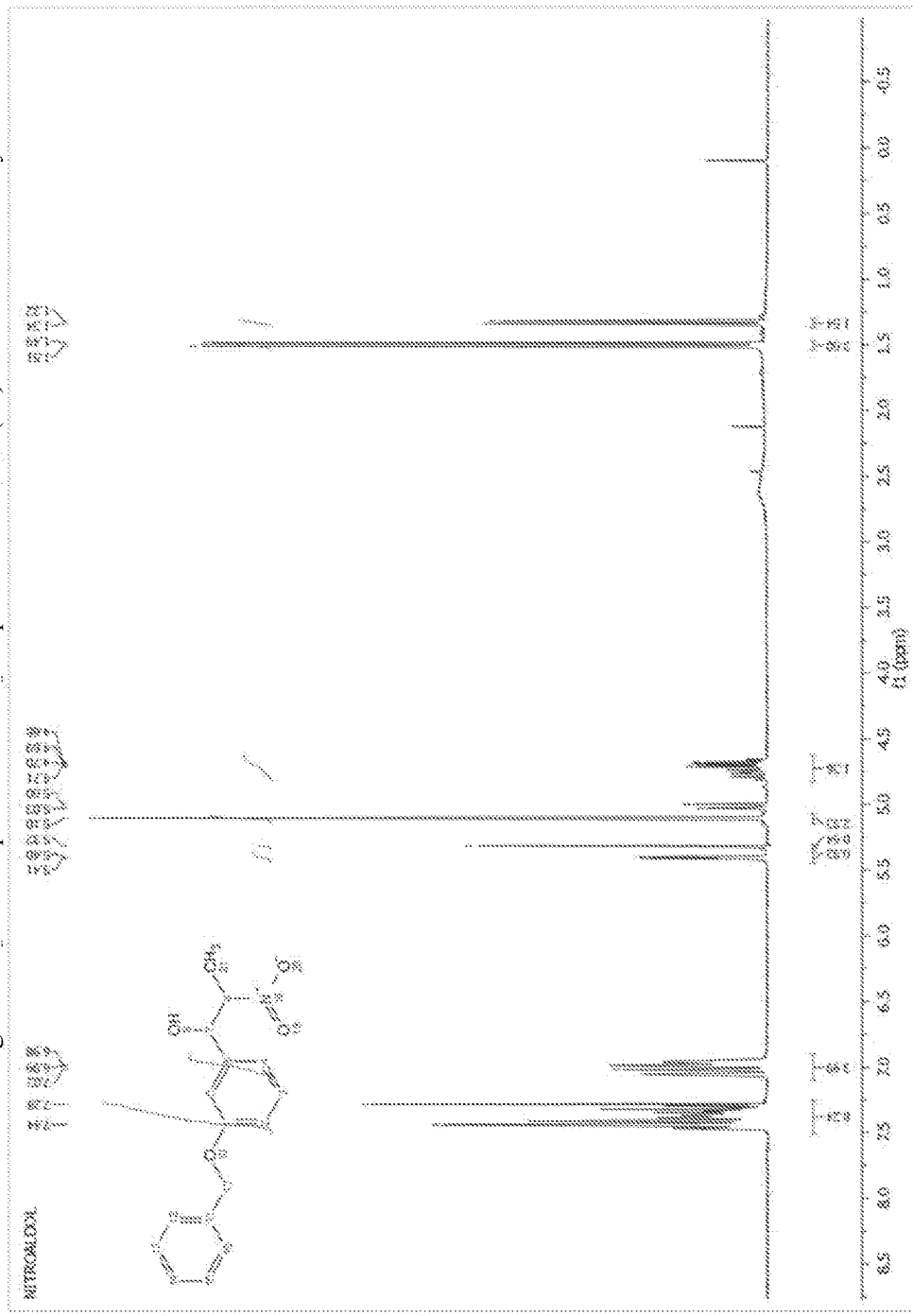
Figure 6: $^1$H-NMR spectrum of the compound of formula (IV) wherein PG is benzyl

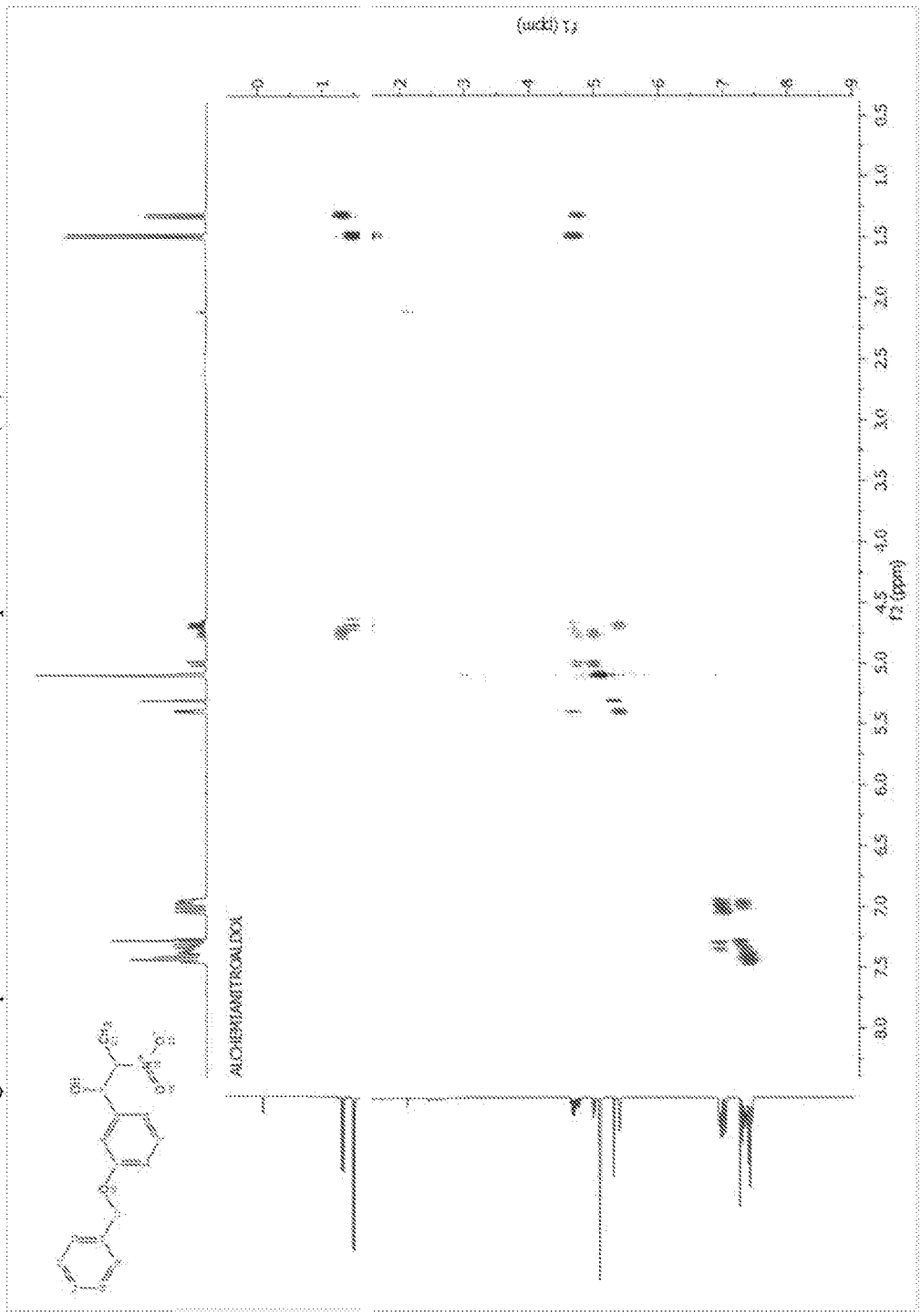
Figure 7: Spettro NMR bidimensionale del composto di formula (IV) dove PG è benzile

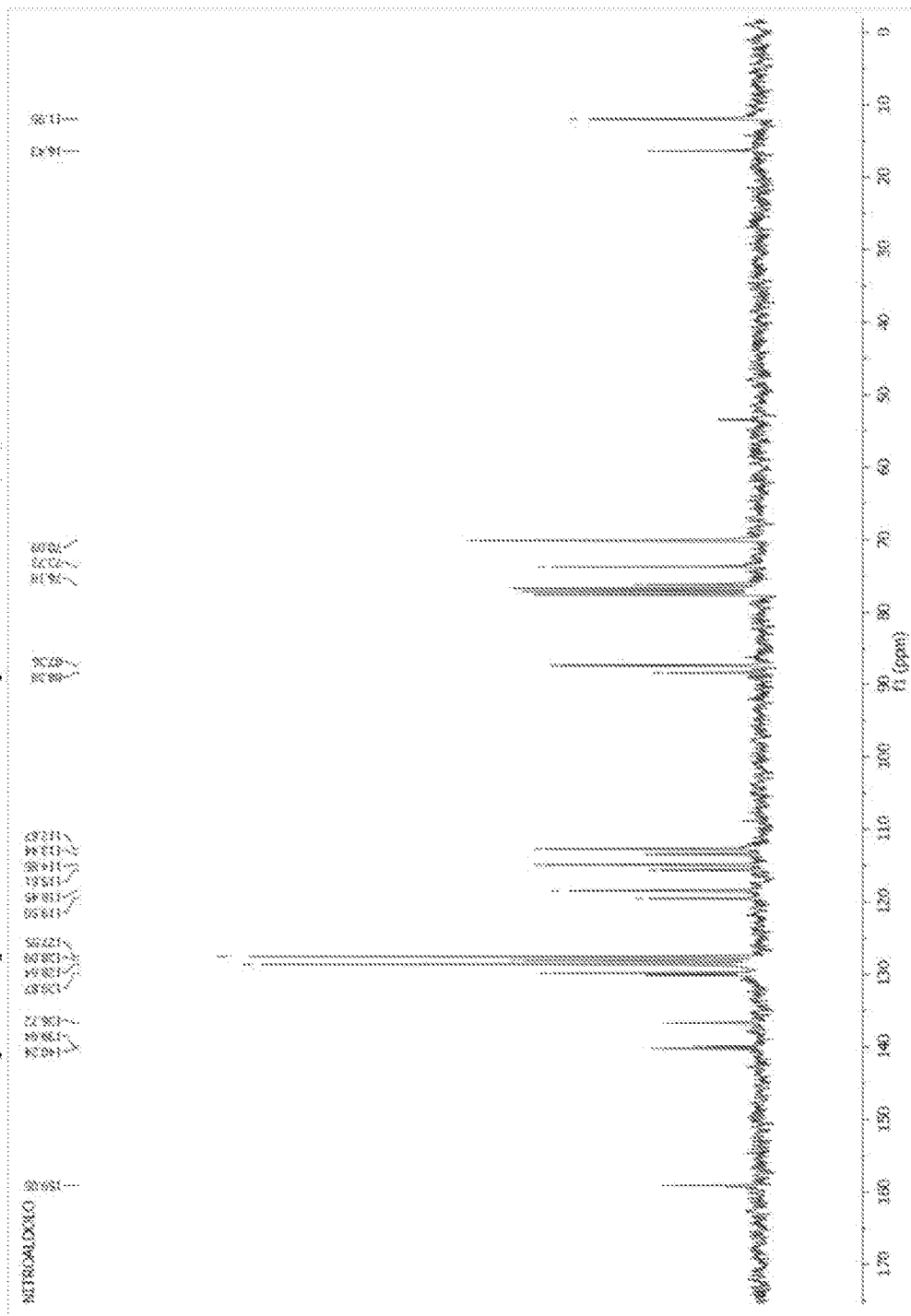
Figure 8: $^{13}$C-NMR spectrum of the compound of formula (IV) wherein PG is benzyl

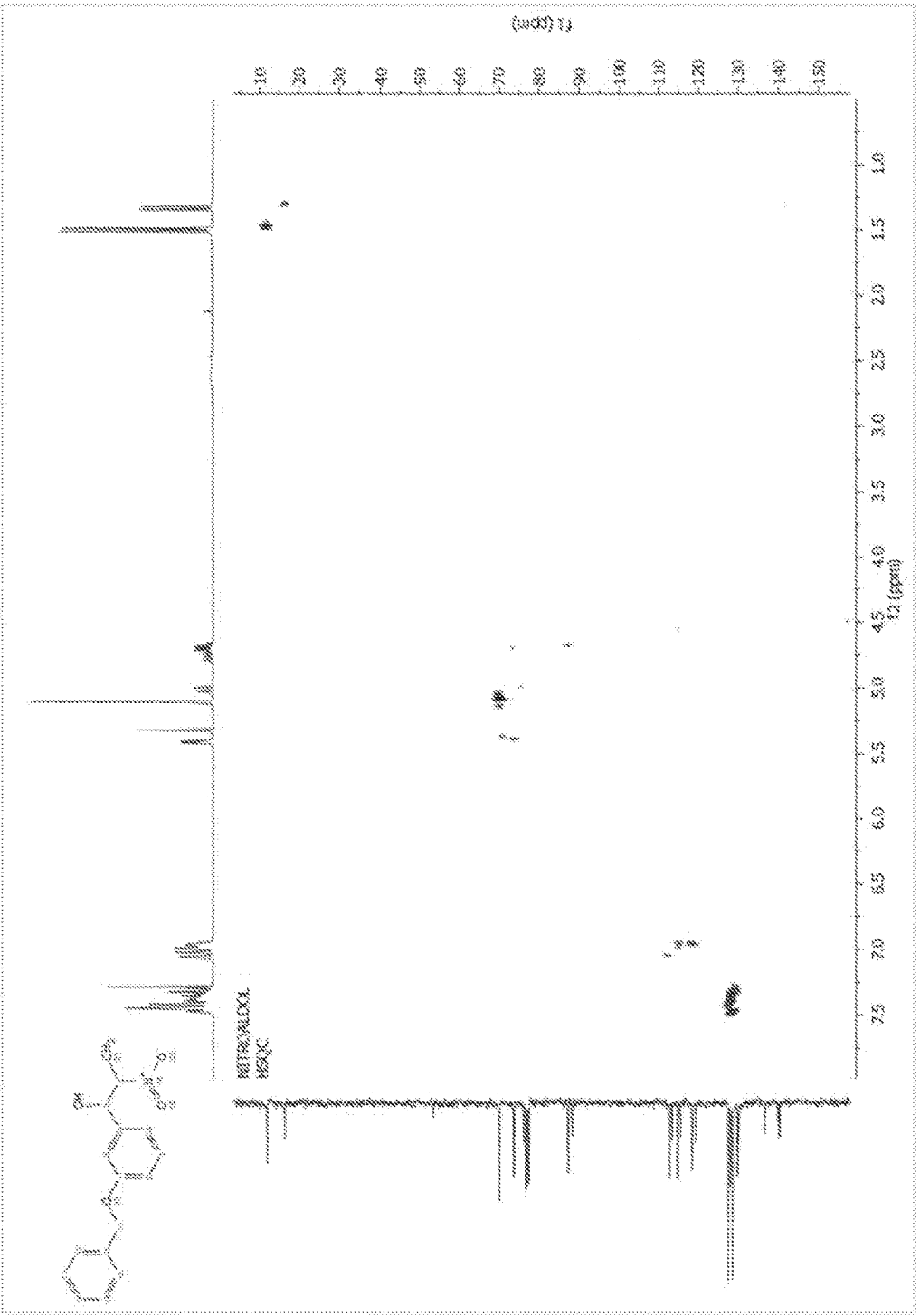
Figure 9: Bidimensional NMR spectrum of the compound of formula (IV) wherein PG is benzyl

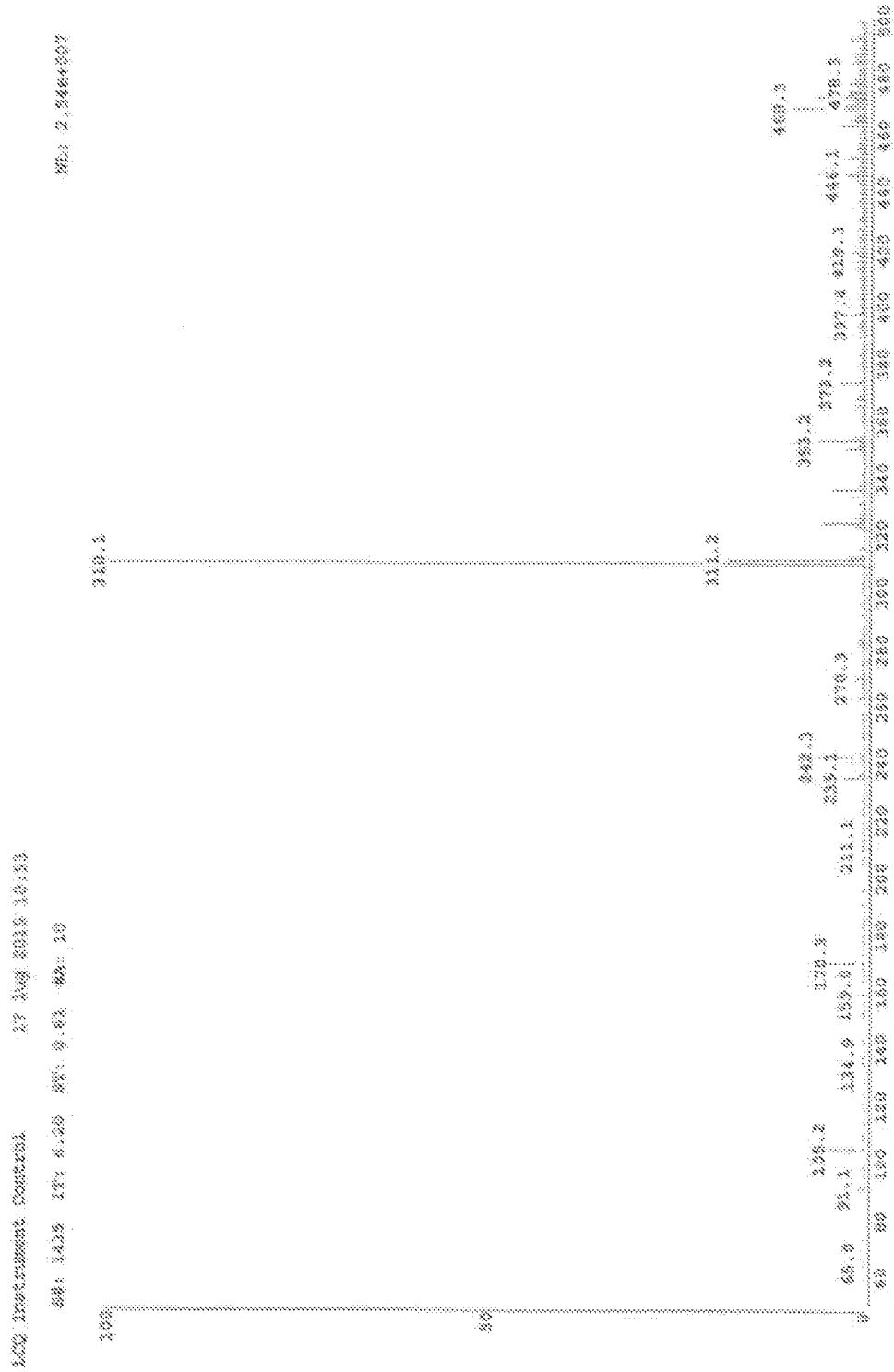
Figure 10: Mass spectrum of the compound of formula (IV) wherein PG is benzyl

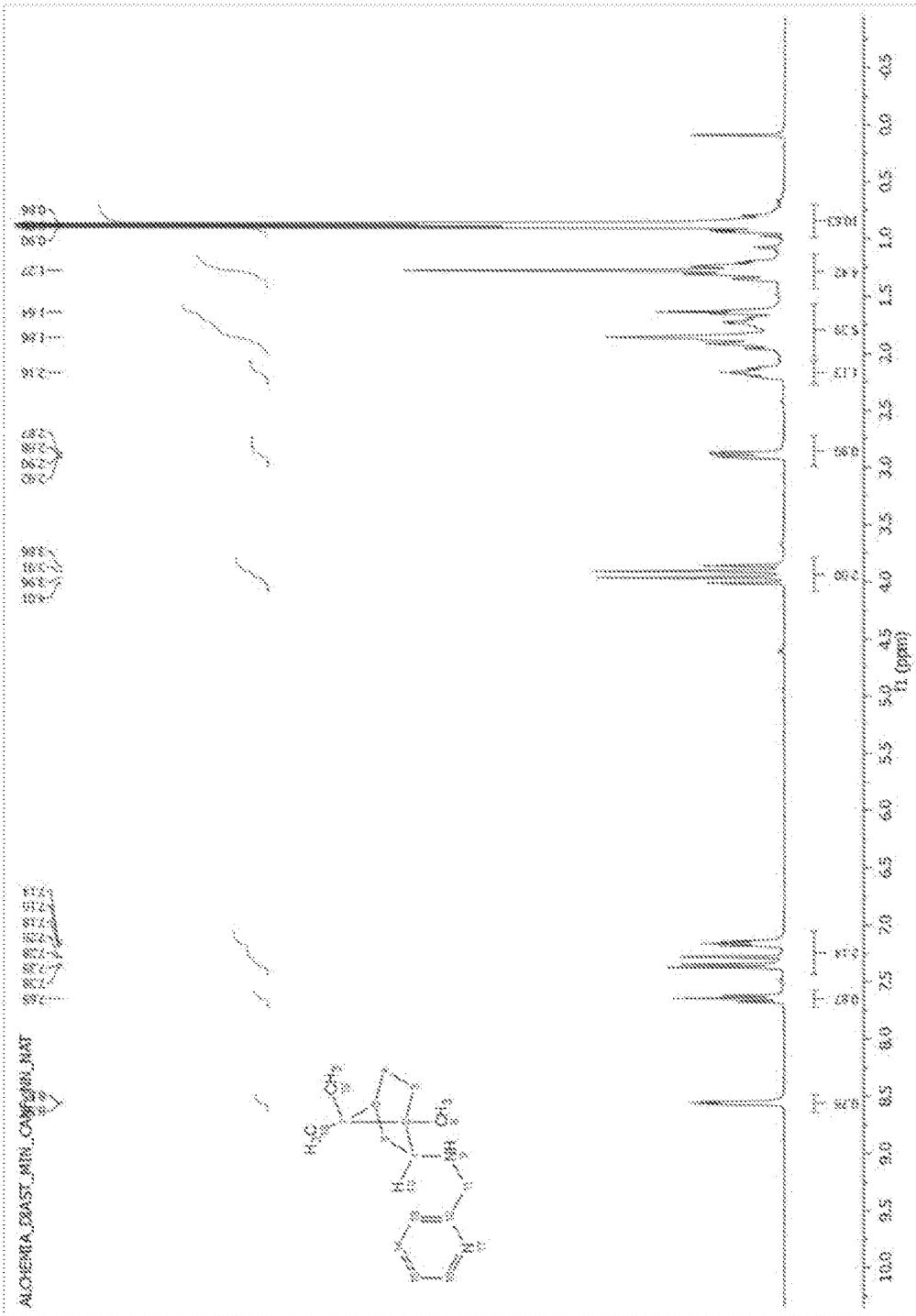
Figure 11: ¹H-NMR spectrum of the intermediate compound of formula (VII)

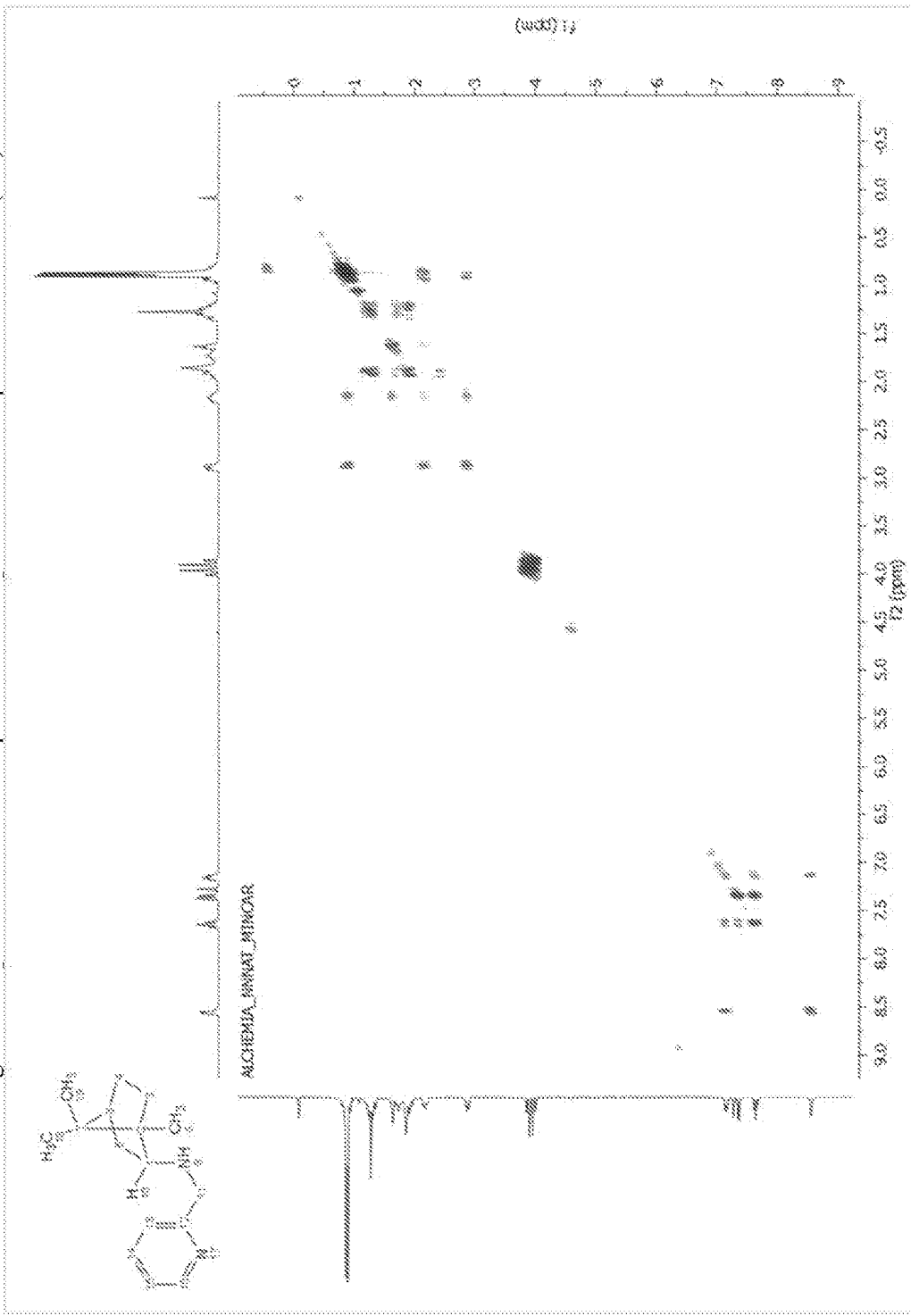
Figure 12: Bidimensional NMR spectrum of the intermediate compound of formula (VII)

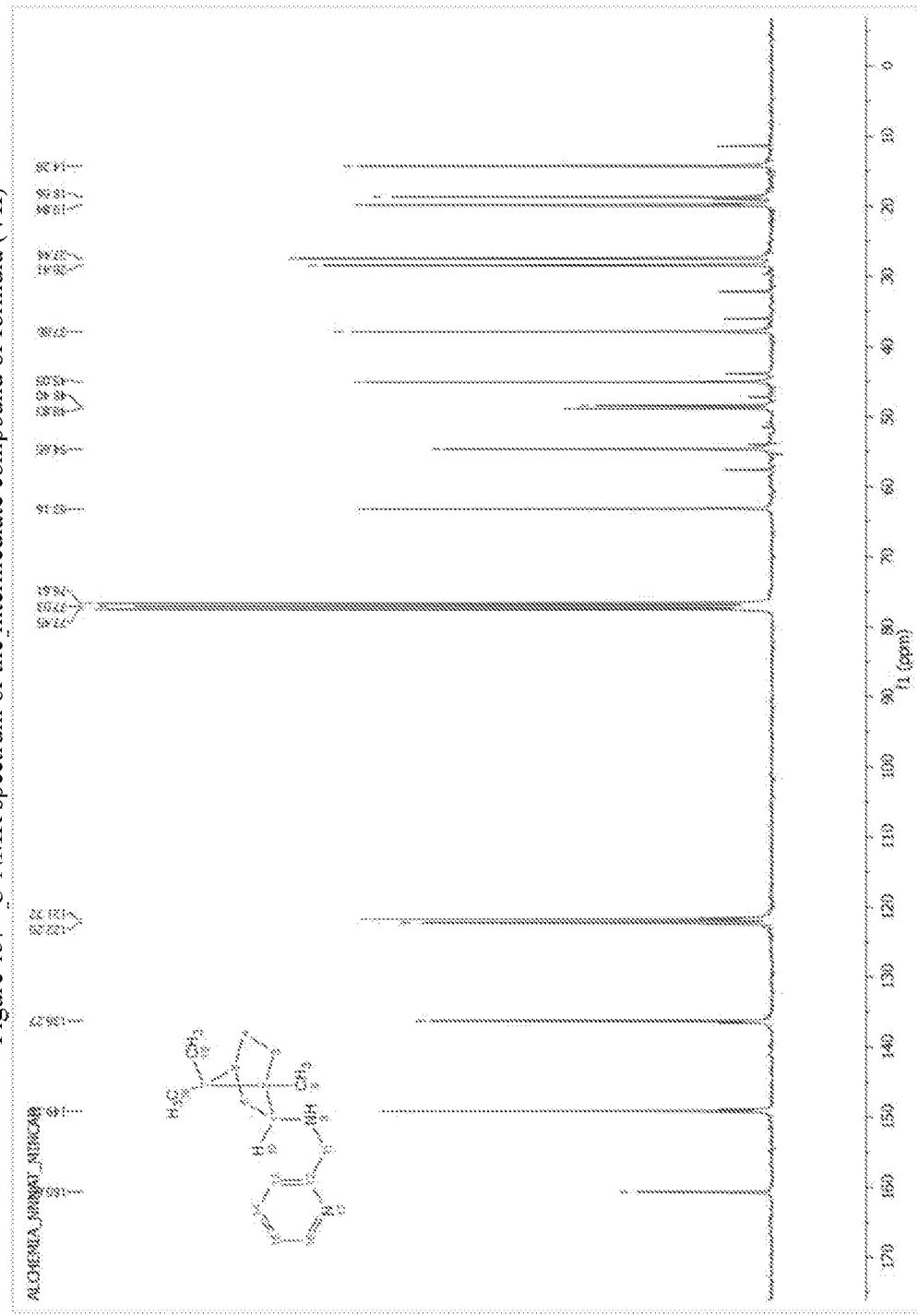
Figure 13: $^{13}$C-NMR spectrum of the intermediate compound of formula (VII)

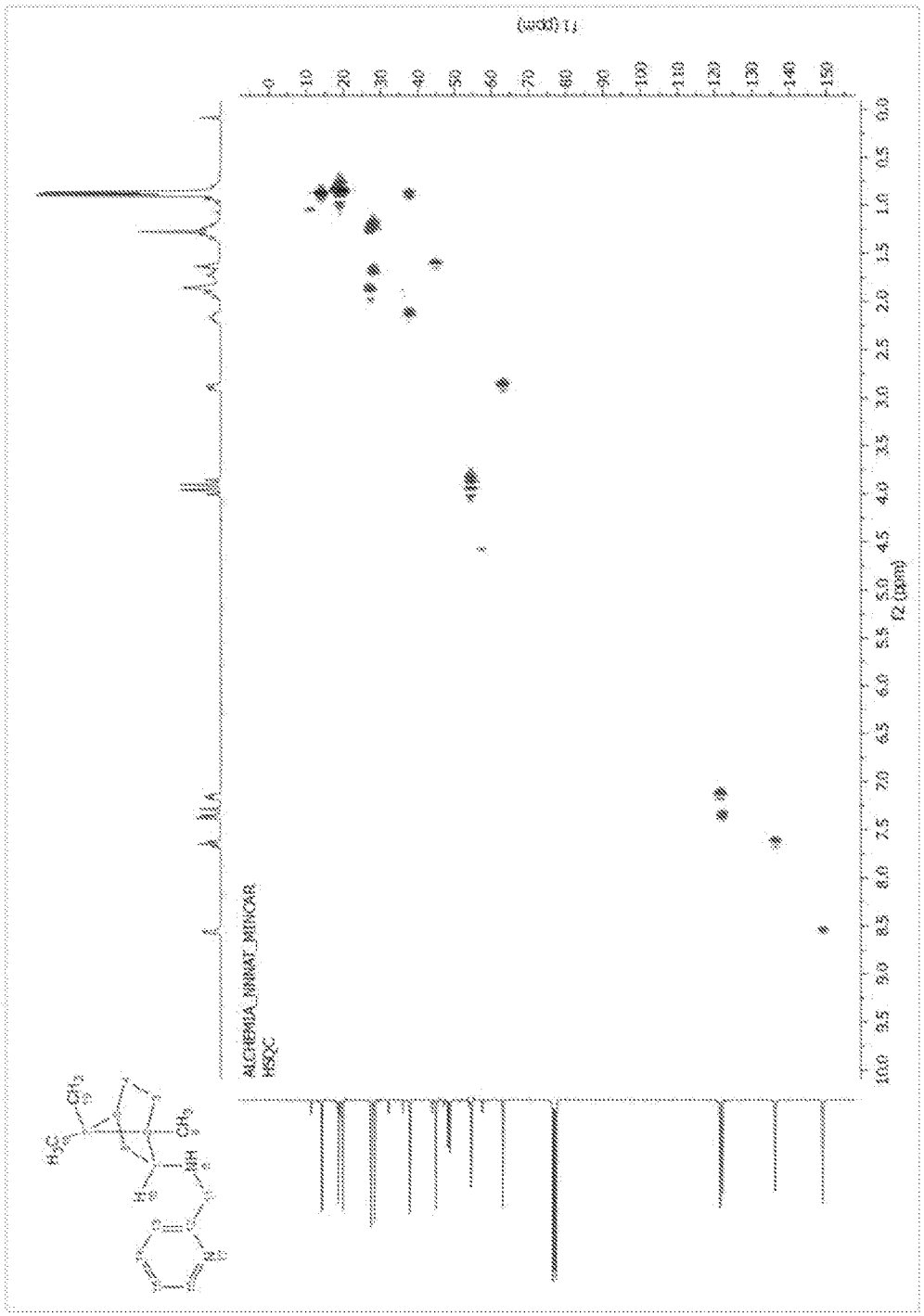
Figure 14: NMR spectrum with heterocorrelation of the intermediate compound of formula (VII)

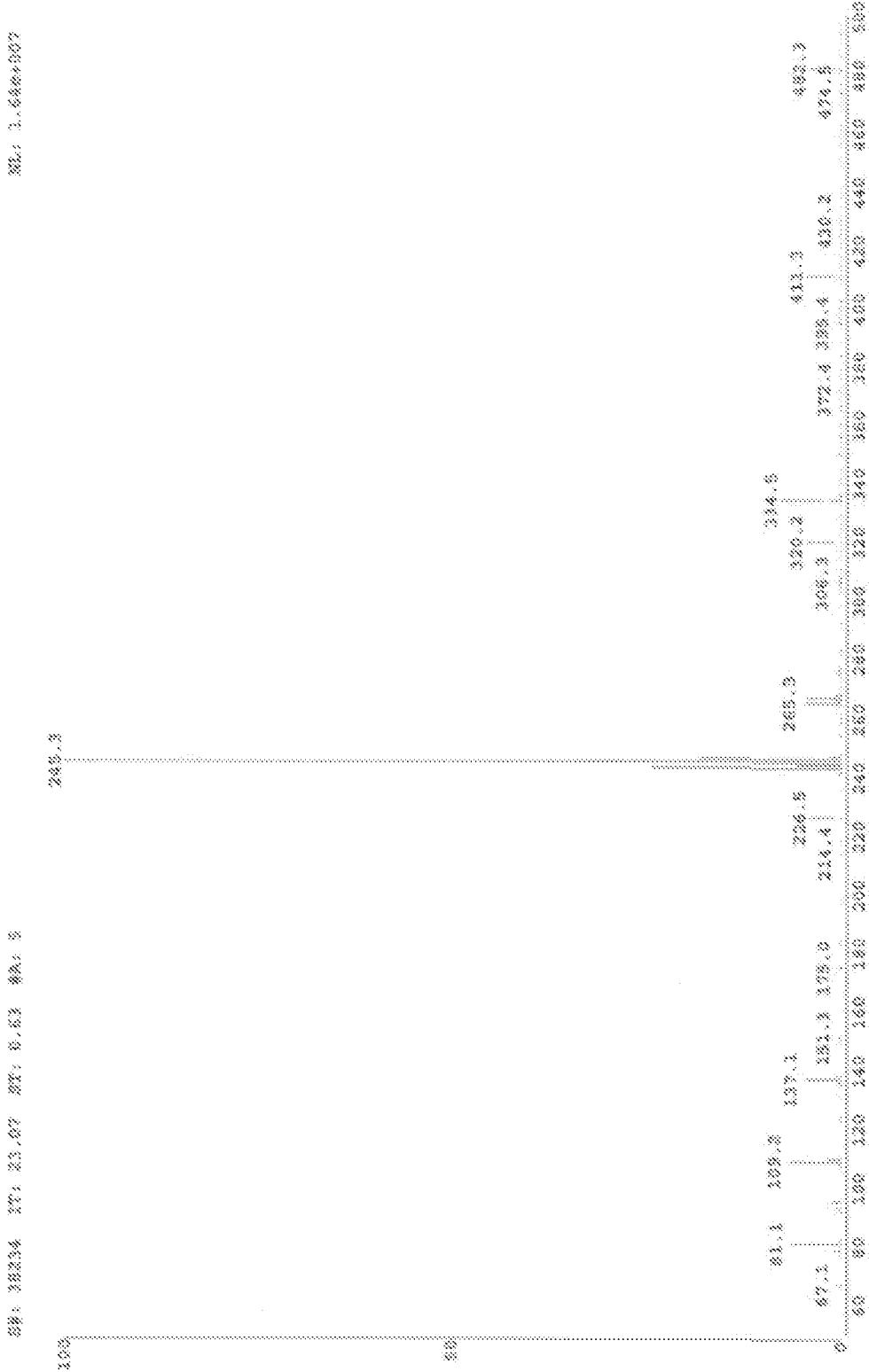
Figure 15: Mass spectrum of the intermediate compound of formula (VII)

PROCESS FOR THE PREPARATION OF METARAMINOL

RELATED APPLICATION

This application claims priority to Italian Application No. 102016000007568 filed 26 Jan. 2016, the contents of which are hereby incorporated by reference as if set forth in their entirety.

SUMMARY OF THE INVENTION

Object of the invention is a process for the preparation of Metaraminol (1R,2S)-3-(2-amino-1-hydroxy-propyl)phenol and the salts thereof, in particular its pharmaceutically acceptable salts, specially Metaraminol bi-L-tartrate. Object of the invention is also the use of a novel catalyst and a novel ligand for the synthesis of Metaraminol and its salts.

BACKGROUND ART

Metaraminol is a life-saving drug which is part of the class of peripheral cardiovascular analeptic drugs. It is a powerful sympathomimetic amine increasing the systolic and diastolic blood pressures. Its effect begins 1-2 minutes after the intravenous administration and about ten minutes after the intramuscular injection and lasts 20 minutes to one hour. Metaraminol has positive inotropic effect at the heart level and vasoconstrictor effect at the peripheral level. Thus, it is indicated for the prevention and treatment of acute hypotensive statuses that may arise, for example, as a result of spinal anesthesia. It is also indicated as additional treatment for hypotension and anaphylactic shock. Metaraminol is currently marketed in the form of its salt with L-tartaric acid (Metaraminol bi-L-tartrate), of the following formula

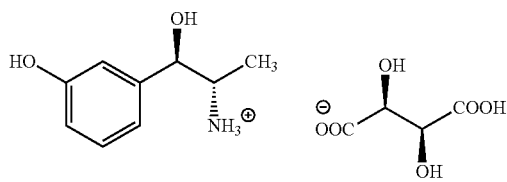

Metaraminol Bi-L-Tartrate

Therefore, Metaraminol bi-L-tartrate is the acidic L-tartrate of a chiral aminoalcohol whose brute formula is $C_9H_{13}NO_2$, with general chemical name of 3-(2-amino-1-hydroxy-propyl)phenol.

Since there are two different stereocenters in the molecule of 3-(2-amino-1-hydroxy-propyl)phenol, four stereoisomers are possible associated in two pairs of enantiomers and are in diastereomeric relation (syn and anti) one to the other:

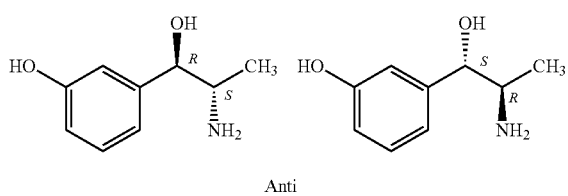

Anti

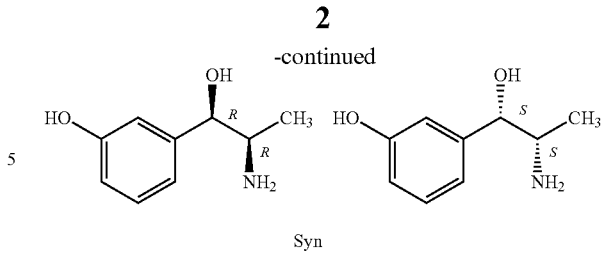

Syn

Metaraminol corresponds to the compound anti "1R,2S" among these four diastereomers and is the only one among the diastereomers showing the high biological activity described above.

Separating enantiomers and diastereomers is known being difficult and expensive. Therefore, there is the continuous need to find new stereoselective syntheses allowing to obtain compounds having more than one stereocenter, such as Metaraminol, not only with optimal yield but above all with satisfying enantiomeric and diastereomeric excesses.

Objects of the Invention

It is an object of the invention to provide a stereoselective synthesis of Metaraminol or one of the salts thereof, in particular Metaraminol bi-L-tartrate, which provides good yields and satisfying diastereomeric and enantiomeric excesses.

It is also an object of the invention to provide the use of a novel metal catalyst and a novel ligand precursor thereof for the synthesis of Metaraminol and the salts thereof.

BRIEF DESCRIPTION OF THE FIGURES

FIG. 1 shows the 1H-NMR spectrum of the compound of formula (III).
FIG. 2 shows the bidimensional NMR spectrum of the compound of formula (III).
FIG. 3 shows the 13C-NMR spectrum of the compound of formula (III).
FIG. 4 shows the NMR spectrum with C—H heterocorrelation of the compound of formula (III).
FIG. 5 shows the mass spectrum of the compound of formula (III).
FIG. 6 shows the 1H-NMR spectrum of the compound of formula (IV) wherein PG is benzyl.
FIG. 7 shows the bidimensional NMR spectrum of the compound of formula (IV) wherein PG is benzyl.
FIG. 8 shows the 13C-NMR spectrum of the compound of formula (IV) wherein PG is benzyl.
FIG. 9 shows the NMR spectrum with C—H heterocorrelation of the compound of formula (IV) wherein PG is benzyl.
FIG. 10 shows the mass spectrum of the compound of formula (IV) wherein PG is benzyl.
FIG. 11 shows the 1H-NMR spectrum of the intermediate compound of formula (VII).
FIG. 12 shows the bidimensional NMR spectrum of the intermediate compound of formula (VII).
FIG. 13 shows the 13C-NMR spectrum of the intermediate compound of formula (VII).
FIG. 14 shows the NMR spectrum with C—H heterocorrelation of the intermediate compound of formula (VII).
FIG. 15 shows the mass spectrum of the intermediate compound of formula (VII).

DESCRIPTION OF THE INVENTION

According to one of its aspects, object of the invention is a process for the preparation of Metaraminol of formula (I)

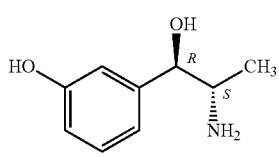

or one of the salts thereof, advantageously a pharmaceutically acceptable salt thereof, in particular bi-L-tartrate salt, comprising subjecting a compound of formula (II)

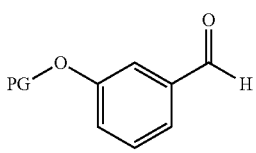

wherein PG is a hydrogen atom or a hydroxy protecting group, to a stereoselective Henry reaction with nitroethane, by using a copper complex with the ligand of formula (III) as a catalyst

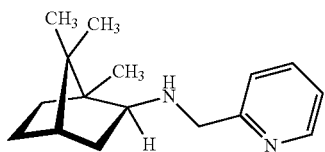

having (S,S,S) configuration of the three stereocenters, reducing the nitro group and deprotecting the so obtained compound of formula (IV)

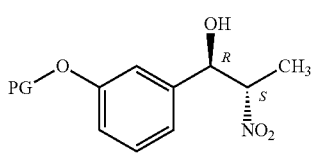

wherein PG is as defined above, to obtain Metaraminol of formula (I) and optionally salifying it, advantageously with L-tartaric acid, to give Metaraminol bi-L-tartrate. According to a preferred embodiment, PG is a hydroxy protecting group.

According to the present invention, by "hydroxy protecting group" herein is meant a group selected among those available according to the know art, such as, for example, the alkoxy groups and the arylalkoxy groups amongst which preferably the benzyloxy group as such or differently substituted, ester groups, included the carbonic acid esters, silylethers, and the like.

According to a preferred embodiment, the Henry reaction is carried out in an organic solvent, advantageously a lower alcohol, for example in a $C_1$-$C_4$ alcohol, preferably 1-propanol, methanol, ethanol, or ether such as THF.

According to a preferred embodiment, the ligand of formula (III) is complexed with bivalent copper prior to the Henry reaction. According to this embodiment, the ligand of formula (III) is dissolved in the reaction solvent, preferably a lower alcohol, for example a $C_1$-$C_4$ alcohol, advantageously 1-propanol and the copper (II) salt is added to the solution, for example $Cu(OAc)_2 \cdot H_2O$, or $Cu(OTf)_2$, the amount of ligand and bivalent copper being preferably equimolar.

The so prepared solution is added to a suspension or solution of the compound of formula (II) containing nitroethane.

Preferably, nitroethane is employed in molar excess to the compound (II), for example 2 to 10 times, preferably a molar excess of about 5 times.

The catalyst constituted by the copper complex and ligand of formula (III) is used in minor amount to the compound of formula (II). By way of example, for 1 equivalent of compound of formula (II), 0.01-0.5 equivalents of catalyst, preferably 0.1 equivalent, can be used.

The reaction is advantageously carried out in the presence of a base, for example a tertiary organic base as triethylamine, diisopropylethylamine, pyridine as such or substituted, that is preferably added in equimolar amounts with respect to the compound (II).

The reaction temperature can range from −5° C. to −70° C., preferably from −20 to −60° C., for example around −40° C. In fact, it has been observed that at temperatures equal or higher than 0° C., a mixture of isomers syn and anti in not very different amounts is obtained, whereas at lower temperatures the desired stereoisomer anti is obtained in higher amounts.

The reaction is completed in some hours and, in general, is completed after 4-48 hours. The expert in the art is anyway able to follow its progress by conventional techniques, for example by chromatography.

At the end of the reaction an acid is added to quench the reaction, for example a solution of hydrochloric acid, and the isolation of the mixture of the four stereoisomers follows, amongst which the compound of formula (IV) is prevailing, according to usual techniques well known to the expert in the art. The same mixture of stereoisomers, without further purification, is then subjected to the reduction step, that provides for the use of reagents available according to the known art for reducing the nitro group, and deprotection step, that provides for the use of specific reagents for removing the used protective group, which are provided for by the known art, to give a mixture of stereoisomers of 3-(2-amino-1-hydroxy-propyl)phenol from which the one with 1R,2S configuration at the two stereocenters (Metaraminol) must be isolated. The sequence of reduction and deprotection steps has no influence on the final result. The reaction of protection of the hydroxyl phenolic function with the benzyl group and deprotection by catalytic hydrogenation is the preferred one.

According to a preferred embodiment, object of the invention is a process for the preparation of Metaraminol comprising the following steps:
  i. preparing a solution of the ligand of formula (III) in a $C_1$-$C_4$ alcohol, advantageously in 1-propanol, and adding copper acetate at a rate of equal equivalents to the ligand of formula (III);
  ii. adding the solution, once it has taken an intense blue coloring, to a suspension of nitroethane and compound (II) cooled to a temperature between −5° C. and −70° C., preferably between −20 and −60° C.;
  iii. adding the base;

iv. quenching the reaction, once complete, with an acidic solution and isolating the mixture of the stereoisomeric nitroalcohols amongst which the compound of formula (IV) is prevailing;
v. reducing and deprotecting the compound of formula (IV) and isolating Metaraminol and/or transforming one of its salts, preferably its bi-L-tartrate salt.

Detailed examples of the process of the invention are described in the Experimental Section of the present description.

Further object of the invention is the use of the ligand of formula (III) and the catalyst obtained by complexing the ligand of formula (III) with transition metals, preferably with copper, advantageously with bivalent copper, in the synthesis of Metaraminol and the salts thereof.

The ligand of formula (III) can be prepared starting from the non-naturally occurring isomer of ((−)-(S,S)-camphor), according to the following Scheme 1:

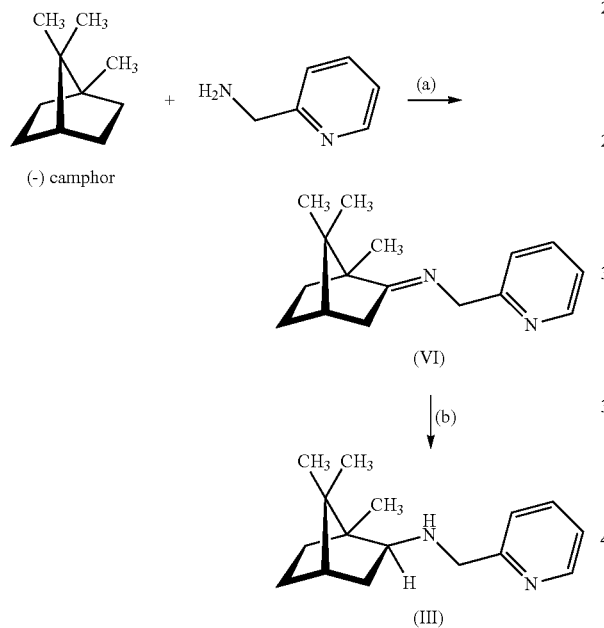

By the reaction of Scheme 1, together with the ligand of formula (III), the diastereomer of formula (VII) having stereocenters with (R,S,S) configuration is obtained at much lesser extent.

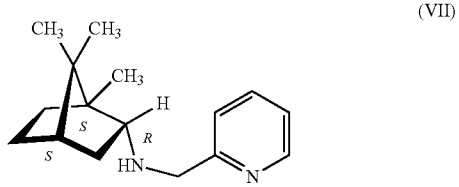

Such a compound can be separated from the compound (III) by the conventional purification techniques, for example by silica gel column chromatography of the crude product of the reaction.

Compounds (III), (IV) and (VII) have been isolated and characterized, as reported in Figures attached to the present description.

Both compounds (III) and (VII) have been tested in the reaction of the process of the invention, in the form of complexes with bivalent copper, as catalysts in the Henry reaction.

The results of said assays, reported in the Experimental Section, showed that only the copper complex with the ligand (III) is effective to favorably catalyze the Henry reaction in order to obtain the desired isomer (R,S), i.e. Metaraminol. In fact, in the Henry reaction reported above, the use of the ligand of formula (III) in the form of complex with copper, provided the isomer (R,S) of the compound of formula (IV) with yields of above 70% to the 4 possible isomers.

Conversely, the compound of formula (VII) didn't prove to be useful to satisfactorily catalyze the Henry reaction from the point of view of the enantiomeric excess.

This result is unexpected and surprising and allows to simply, economically and industrially feasibly synthesizing Metaraminol.

Further object of the invention is Metaraminol, in particular Metaraminol bi-L-tartrate obtained by the process of the invention.

EXPERIMENTAL SECTION

Example 1

General Procedure for the Stereoselective Henry Reaction

To a solution of ligand (III) (0.1 eq) dissolved in 1-propanol (0.6M) Cu(OAc)$_2$.H$_2$O (0.1 eq) is added. The mixture is stirred at rt for 40 minutes, then is added to a suspension of aldehyde (II) (1 eq) in 1-propanol (0.5M). After 5 minutes waiting, then nitroethane (5 eq) is added and, after further 5 minutes stirring, triethylamine (1 eq) is quickly dripped. The mixture is left under stirring at the reaction temperature for the time indicated. The reaction is stopped by adding 7N HCl in isopropanol (2.2 eq). The volatile fraction is evaporated at 50° C. under low vacuum. The residue is taken up with ethyl acetate and 4 extractions are made with an aqueous solution of 2N HCl. The organic phase is washed with brine, dried with MgSO$_4$ and the solvent is removed at reduced pressure. The desired product is obtained as low melting, waxy solid.

| Test | L* | Cu eq | L* eq | Solvent | Temp °C. | Time hours | Yield % | Ratio anti/syn | ee % (IV) | Yield % (IV) |
|---|---|---|---|---|---|---|---|---|---|---|
| 1 | (III) | 0.10 | 0.10 | n-PrOH | −40 | 6 | 99 | 83/17 | 99 | 82 |
| 2 | (III) | 0.05 | 0.05 | EtOH | −45 | 24 | 99 | 75/25 | 92 | 71 |
| 3 | (III) | 0.10 | 0.10 | i-PrOH | −45 | 6 | 93 | 72/28 | 88 | 61 |
| 4 | (VII) | 0.10 | 0.10 | i-PrOH | −45 | 24 | 99 | 72/28 | racemic | 34 |

L* = ligand; EtOH = ethanol; i-PrOH = i-propanol; n-PrOH = 1-propanol

It can be noted that by the tests made the desired stereoisomer (1R,2S) of the compound (IV), direct precursor of Metaraminol, is obtained in excellent yields, good diastereoselection and optimal enantioselection. In the best conditions, it is formed with a yield of 82% to the four possible isomers.

From the test 4 it is observed that, by using the ligand of formula (VII), no type of enantioselection is made and the desired product is formed with a yield of 34% only. Finally, from the tests performed, it is deducted that the temperature is a critical factor for the good success of the reaction.

Example 2

Deprotection/Reduction Example

To a solution of compound (IV) in methanol (0.9M), then wet Pd/C 5% (10%) was added. It is high-pressure hydrogenated (10-100 atm) at a temperature between 18 and 40° C. until completion of the hydrogenolysis reaction of the protecting group and the reduction reaction of the nitro group (6-24 hours). The catalyst is filtered and the solvent removed at low pressure. The compound (IV) is obtained as a low melting, glassy solid, in yield of 85-100%.

Example 3

Preparation of Metaraminol Bi-L-Tartrate

L-tartaric acid is dissolved in methanol (1.3M) and a solution of compound (IV) in methanol (0.7M) is quickly added. The solid is allowed precipitating, and then half of the solvent is removed at reduced pressure. Crude Metaraminol bi-L-tartrate is isolated by filtration. The latter is crystallized from absolute ethanol in a 1:80 w/v ratio, obtaining pure Metaraminol bi-L-tartrate in yield of 35-70%.

Preparation of the Ligand (−)-camphor (1 eq) and 2-picolylamine (1 eq) are dissolved in toluene (1.6M each reagent), then p-toluenesulfonic acid (0.1 eq) is added. The mixture is heated at reflux, by separating the distilling water. After 4 hours it is cooled to room temperature and the organic solution is washed with an aqueous solution of sodium bicarbonate, then with water. It is anhydrified with magnesium sulfate and the organic solvent is removed at reduced pressure, obtaining the compound (VI) as yellow oil.

Sodium borohydride (16 eq) is suspended in THF, and a solution of compound (VI) dissolved in methanol (0.1M) is slowly dripped at 0° C. After 24 hours aqueous concentrated hydrochloric acid is dripped until complete destruction of the excess of sodium borohydride. The organic solvent is removed at reduced pressure, then aqueous sodium hydroxide until pH=12 is added to the mixture. The desired product is extracted by washing with dichloromethane. The organic phase is anhydrified and the organic solvent is removed at low pressure, obtaining the crude compound (III).

It is purified by low pressure distillation, obtaining a mixture of compounds (III) and (VI) in a proportion of about 5:1, as pale yellow oil (yield: 64%).

The invention claimed is:

1. A process for preparation of Metaraminol of formula (I)

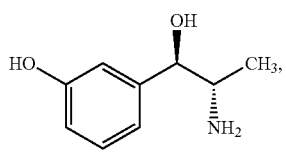

(I)

comprising subjecting a compound of formula (II)

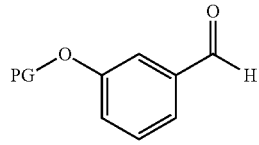

(II)

wherein PG is a hydrogen atom or a hydroxy protecting group, to a stereoselective Henry reaction with nitroethane, by using a copper complex with a ligand of formula (III) as a catalyst

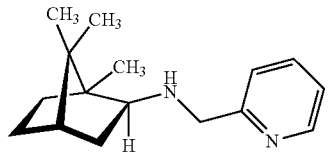

(III)

in the (S,S,S) configuration, said ligand of formula (III) being prepared starting from a non-naturally occurring isomer of ((−)-(s,s) camphor), and reducing and deprotecting a compound of formula (IV)

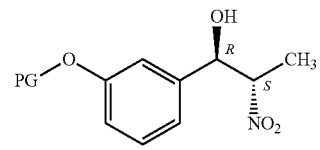

(IV)

produced by said stereoselective Henry reaction, to obtain said Metaraminol of formula (I).

2. The process according to claim 1, further comprising converting the Metaraminol of formula (I) to Metaraminol bi-L-tartrate.

3. The process according to claim 1, wherein the ligand of formula (III) is dissolved in a solvent, said solvent comprising a lower alcohol or an ether.

4. The process according to claim 3, wherein said solvent is one of ethanol and n-propanol.

5. The process according to claim 1, wherein said PG comprises said hydroxy protecting group.

6. The process according to claim 1, wherein said ligand of formula (III) is complexed with bivalent copper.

7. The process according to claim 1, wherein said nitroethane is present in molar excess to the compound of formula (II).

8. The process according to claim 1, wherein the Henry reaction is carried out in the presence of a base.

9. The process according to claim 1, wherein a temperature of the Henry reaction is from −5° C. to −70° C.

10. A process for preparation of Metaraminol comprising:

preparing a solution of a ligand of formula (III) in a $C_1$-$C_4$ alcohol, and adding copper acetate at a rate of equal equivalents to the ligand of formula (III);

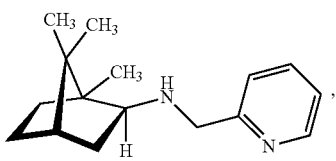
(III)

said ligand of formula (III) in the (S,S,S) configuration being prepared starting from a non-naturally occurring isomer of ((−)-(s,s) camphor), adding the solution, once it has taken an intense blue coloring, to a suspension of nitroethane and compound (II) cooled to a temperature between −5° C. and −70° C.,

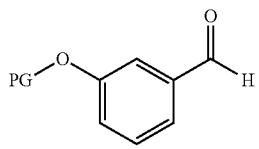
(II)

adding a base;

after said adding the solution and said adding a base, quenching; with an acidic solution and isolating a mixture of stereoisomeric nitroalcohols in which a compound of formula (IV) forms a majority thereof;

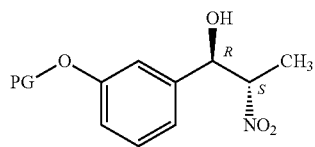
(IV)

reducing and deprotecting the compound of formula (IV) and isolating Metaraminol.

11. A process comprising:

providing a composition, said composition being a ligand of formula (III)

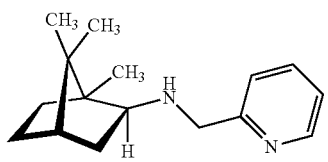
(III)

in the (S,S,S) configuration, or a salt thereof or a complex thereof with copper, and using said composition in the preparation of Metaraminol or a salt thereof.

12. The process for preparation of Metaraminol according to claim 10, wherein said $C_1$-$C_4$ alcohol comprises 1-propanol.

13. The process for preparation of Metaraminol according to claim 10, wherein said temperature is between −20 and −60° C.

14. The process for preparation of Metaraminol according to claim 10, further comprising transforming said Metaraminol into a salt thereof.

15. The process for preparation of Metaraminol according to claim 14, wherein said salt comprises a bi-L-tartrate salt of said Metaraminol.

16. The process according to claim 1, further comprising converting said Metaraminol of formula (I) to a salt thereof.

* * * * *